US008034368B2

(12) United States Patent
Myers et al.

(10) Patent No.: US 8,034,368 B2
(45) Date of Patent: Oct. 11, 2011

(54) DRUG DELIVERY DEVICE FOR PROVIDING LOCAL ANALGESIA, LOCAL ANESTHESIA OR NERVE BLOCKAGE

(75) Inventors: Michael Myers, Ashburn, VA (US); Philip Wallace Reginald, Farnham Common (GB)

(73) Assignee: Innocoll Technologies Limited, County Roscommon (IE)

( * ) Notice: Subject to any disclaimer, the term of this patent is extended or adjusted under 35 U.S.C. 154(b) by 784 days.

(21) Appl. No.: 12/058,298

(22) Filed: Mar. 28, 2008

(65) Prior Publication Data

US 2008/0241245 A1 Oct. 2, 2008

Related U.S. Application Data

(63) Continuation-in-part of application No. 11/692,337, filed on Mar. 28, 2007, now abandoned.

(51) Int. Cl.
*A61F 2/02* (2006.01)
(52) U.S. Cl. ........................................................ 424/426
(58) Field of Classification Search ........................ None
See application file for complete search history.

(56) References Cited

U.S. PATENT DOCUMENTS

2006/0280801 A1 12/2006 Kronenthal

FOREIGN PATENT DOCUMENTS

IE 53579 6/1981

OTHER PUBLICATIONS

Friess, "Collagen—Biomaterial for Drug Delivery", European Journal of Pharmaceutics or Biopharmaceutics, vol. 45, Issue 2, Mar. 1998, pp. 113-136.*
Bartholdy et al., "Preoperative infiltration of the surgical area enhances postoperative analgesia of a combined low-dose epidural bupivacaine and morphine regimen after upper abdominal surgery", Acta Anaesthesiologica Scandinavica 1994 38:262-265.
Cobby et al., "Wound infiltration with local anaesthetic after abdominal hysterectomy", British Journal of Anaesthesia 1997 78:431-432.
Gupta et al., "Postoperative Pain After Abdominal Hysterectomy:A Double-Blind Comparison Between Placebo and Local Anesthetic Infused Intraperitoneally", Anesth Analg 2004 99:1173-1179.
Hannibal et al., "Preoperative Wound Infiltration with Bupivacaine Reduces Early and Late Opioid Requirement After Hysterectomy", Anesth Analg 1996 83:376-381.

(Continued)

*Primary Examiner* — Carlos Azpuru
(74) *Attorney, Agent, or Firm* — Licata & Tyrrell P.C.

(57) ABSTRACT

The invention relates to a drug delivery device for providing local analgesia, local anesthesia or nerve blockage at a site in a human or animal in need thereof, the device comprising a fibrillar collagen matrix; and at least one drug substance selected from the group consisting of amino amide anesthetics, amino ester anesthetics and mixtures thereof, the at least one drug substance being substantially homogeneously dispersed in the collagen matrix, and the at least one drug substance being present in an amount sufficient to provide a duration of local analgesia, local anesthesia or nerve blockade which lasts for at least about one day after administration.

23 Claims, 2 Drawing Sheets

OTHER PUBLICATIONS

Klein et al., "Infiltration of the abdonimal wall with local anaesthetic after total abdominal hysterectomy has no opioid-sparing effect", British Journal fo Anaesthesia 2000 84(2):248-249.

Leung et al. "Effect of Pre-Incision Skin Infiltration on Post-Hysterectomy Pain-A Double-Glind Randomized Controlled Trial", Anaesth Intensive Care 2000 28:510-516.

Moiniche et al., "A qualitative systematic review of incisional local anaesthesia for postoperative pain relief after abdonimal operations", British Journal of Anaesthesia 1998 81:377-383.

Ng et al., "The Analgesic Effects of Intraperitoneal and Incisional Bupivacaine with Epinephrine After Total Abdonimal Hysterectomy", Anesth Analg 2002 95:158-162.

Sinclair et al., "Postoperative pain relief by topical lidocaine in the surigcal wound of hysterectomized patients", Acta Anaesthesiologica Scandinavica 1996 40:589-954.

Victory et al., "Effect of Preincision versus Postincision Infiltration with Bupivacaine on Postoperative Pain", Journal of Clinical Anesthesia 1995 7:192-196.

* cited by examiner

Figure 1      Flow Diagram for Production of Collagen
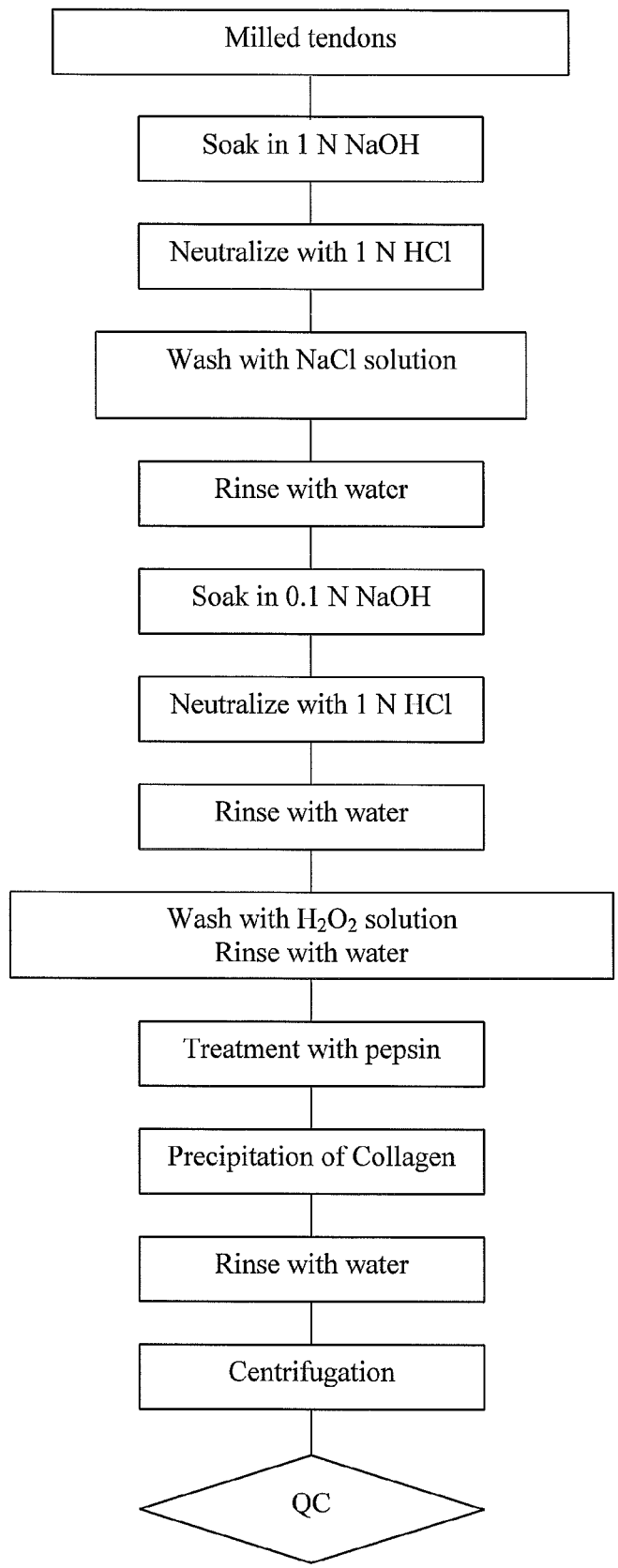

Figure 2   Flow Diagram for Production of Bupivacaine-Collagen Sponge
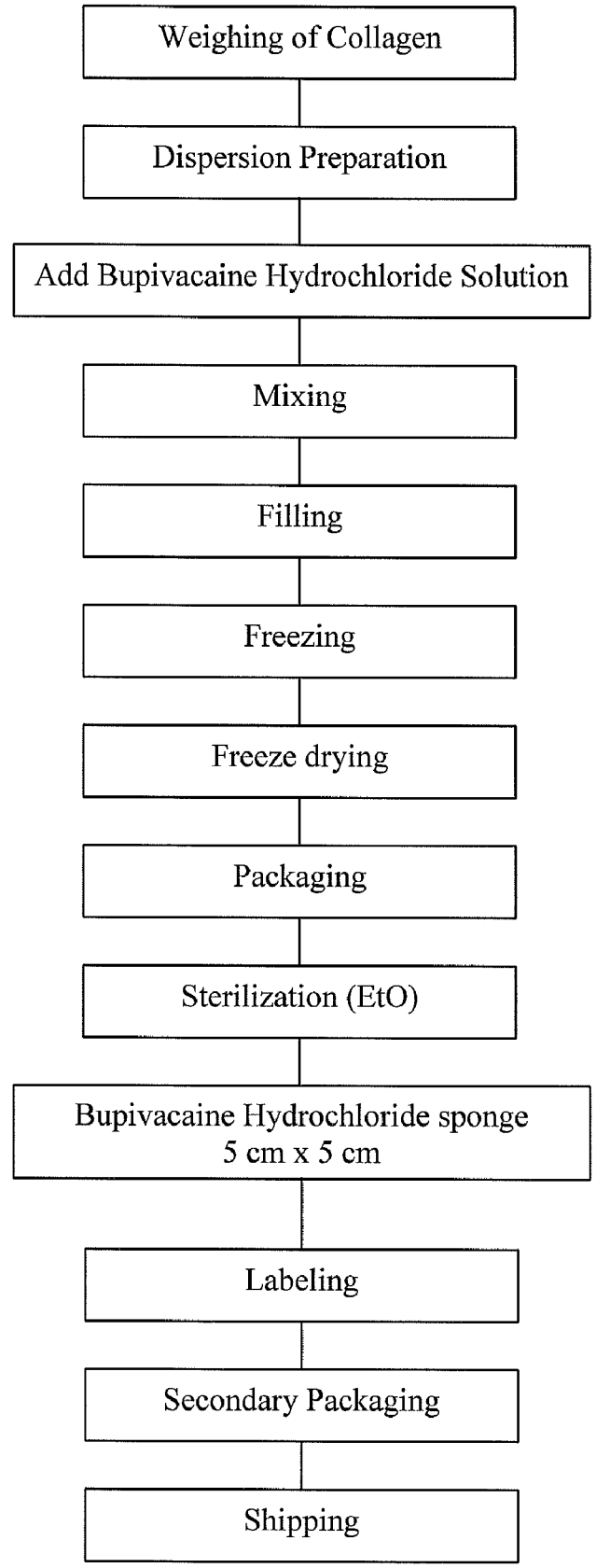

DRUG DELIVERY DEVICE FOR PROVIDING LOCAL ANALGESIA, LOCAL ANESTHESIA OR NERVE BLOCKAGE

INTRODUCTION

This application is a continuation-in-part of U.S. Ser. No. 11/692,337 filed Mar. 28, 2007 now abandoned, which is herein incorporated by reference in its entirety.

FIELD OF THE INVENTION

The present invention relates to a drug delivery device for providing local analgesia, local anesthesia or nerve blockade and a method for providing local analgesia, local anesthesia or nerve blockade in a human or animal in need thereof.

RELATED BACKGROUND ART

Post-surgical pain is a complex response to tissue trauma during surgery that stimulates hypersensitivity of the central nervous system. Post-operative pain increases the possibility of post-surgical complications, raises the cost of medical care and, most importantly, interferes with recovery and return to normal activities of daily living. Management of post-surgical pain is a basic patient right. When pain is controlled or removed, a patient is better able to participate in activities such as walking or eating, which will encourage his or her recovery. Patients will also sleep better, which aids the healing process.

Collagen sponges have been used globally as hemostatic agents. The present inventors have developed a drug delivery device in the optional form of a collagen sponge impregnated with at least one anesthetic such as bupivacaine hydrochloride, intended for use in the management of post-operative pain following surgery including, but not limited to, moderate/major orthopedic, abdominal, gynecological or thoracic surgery. The at least one anesthetic is contained, in one embodiment, within a collagen matrix comprised of fibrillar collagen, such as Type I collagen purified from bovine Achilles tendons.

Bupivacaine, introduced in 1963, is a widely used amide local anesthetic with a prolonged duration of action. It affects sensory nerves more than motor nerves and can also be used to provide several days' effective analgesia without motor blockade.

Bupivacaine is characterized by its longer duration and slow onset compared with other local anesthetics. Bupivacaine is markedly cardiotoxic. Systemic exposure to excessive quantities of bupivacaine mainly result in central nervous system (CNS) and cardiovascular effects—CNS effects usually occur at lower blood plasma concentrations and additional cardiovascular effects present at higher concentrations, though cardiovascular collapse may also occur with low concentrations. CNS effects may include CNS excitation (nervousness, tingling around the mouth, tinnitus, tremor, dizziness, blurred vision, seizures) followed by depression (drowsiness, loss of consciousness, respiratory depression and apnea). Cardiovascular effects include hypotension, bradycardia, arrhythmias, and/or cardiac arrest—some of which may be due to hypoxemia secondary to respiratory depression.

Incisional Local Anesthesia

Wound infiltration with local anesthesia is used widely for postoperative pain: it is simple, safe and low cost. However, it is unclear whether differences in surgical procedure or whether visceral components influence efficacy. Incisional anesthesia includes infiltration, topical administration or instillation of local anesthetic at the following sites: skin, subcutaneous tissue, fascia, muscle and/or the parietal peritoneum. However, in spite of widespread use, wound infiltration is still inconsistently and randomly used by many surgeons and anesthetists.

Although there is a great number of papers and reviews on this topic, there is little consensus available on when and after which surgical procedures, incisional local anesthesia may provide clinically relevant post-operative pain alleviation. Of special interest may be to what extent differences in surgical procedure or involvement of visceral components influence efficacy. Incisional local anesthesia has been studied in a broad range of surgical models, including abdominal hysterectomy, inguinal herniotomy, open cholecystectomy, appendectomy, Caesarian section and other laparotomy procedures. A laparotomy is a surgical maneuver involving an incision through the abdominal wall to gain access into the abdominal cavity.

The anesthetics assessed for post-operative pain relief include lidocaine, bupivacaine, ropivacaine and mepivacaine, which all belong to the amino amide anesthetic group. On review of the data on the use of incisional anesthesia in hysterectomy surgery, conflicting results have been obtained. In a study by Sinclair et al, 1996, 500 mg of lidocaine administered as an aerosol subcutaneously caused a significant reduction of approximately 50% in pain scores and supplementary analgesic consumption during the first 24 hours of the study, but not later. In a study by Hannibal and co-workers, 0.25% bupivacaine solution 45 ml infiltrated subfascially and subcutaneously caused a 50% reduction in analgesic consumption but not in pain scores or time to first analgesic request. In contrast, two studies evaluating subcutaneous infiltration of bupivacaine solution compared with no treatment showed no improvement in analgesia (Cobby et al, 1997, Victory et al, 1995).

Studies in other models have shown short-term analgesic effects over 4 to 7 hours. In three studies on Caesarian section, 0.25% or 0.5% bupivacaine 20 ml caused a 20-50% reduction in analgesic consumption but this effect only lasted for 4 hours. In another study in upper abdominal surgery, only a slight reduction in daily morphine administration (supplemental intramuscular morphine) (10 mg) was noted and a reduction in visual analogue scoring (VAS) only during mobilization was recorded (50 mm) (Bartholdy et al, 1994). In a review of incisional anesthesia for the control of post-operative pain, Møiniche et al (1998) assessed 26 studies involving over 1200 patients in surgeries using abdominal incision. The results showed a consistent statistical and clinical effect of incisional anesthesia in herniotomy surgery, although the analgesia was short-lived (2-7 hours). However, in the other surgical models evaluated including hysterectomy the results were variable between studies.

Of the 26 studies evaluated (Møiniche et al, 1998), eight were unequivocally negative. Although the majority of studies showed significant differences in at least one pain measure, several were of questionable clinical importance and the authors were surprised that local anesthesia was not associated with more consistent positive results. The authors also noted the importance in the technique used and site to administer the anesthetics.

Since the 1998 review, surgical wound infiltration trials have continued to be performed and published as the practice remains relatively common despite the lack of strong evidence. For example, a group in Leicester, UK, has published two hysterectomy trials (Klein et al, 2000 and Ng et al, 2002), which at best have concluded a duration of effect only up to 4 hours post-operatively.

In contrast, trials where bupivacaine has been instilled post-operatively on a continuous or intermittent basis via an indwelling catheter have tended to prove much more successful and effective. Gupta et al (2004) compared an infusion of normal saline against an infusion of 0.25% levobupivacaine (12.5 mg/hr) over 24 hours and showed a significant reduction in incisional pain, deep pain and pain on coughing at 1-2 hours post hysterectomy surgery. Total ketobemidone (PCA narcotic) was significantly reduced over the 4-24 hour period and the authors conclude that the intraperitoneal infusion of levobupivacaine has significant opioid sparing effects after elective abdominal hysterectomy.

The apparent efficacy of anesthetic infusions explains the widespread use of ambulatory pain pumps, such as I-Flow's ON-Q® Painbuster. However, such continuous infusion devices use much higher total doses of bupivacaine (between 2.5 mg/hr and 50 mg/hr with a maximum dosing duration of 5 and 2 days, respectively) and of course are less convenient than a biodegradable implant. The in-dwelling catheter used in the pain pump system can lead to infection and must be removed by a physician or nurse. In contrast, a drug delivery device such as the bupivacaine-collagen sponge provides, as will be demonstrated hereunder, effective, long lasting analgesia but at a dose only equivalent to a once-off bolus infiltration of the wound.

In the present invention, this long lasting analgesia is achieved through the use of a drug delivery device for providing local analgesia, local anesthesia or nerve blockade at a site in a human or animal in need thereof, the device comprising a fibrillar collagen matrix; and at least one drug substance selected from the group consisting of amino amide anesthetics, amino ester anesthetics and mixtures thereof, the at least one drug substance being substantially homogeneously dispersed in the collagen matrix, and the at least one drug substance being present in an amount sufficient to provide a duration of local analgesia, local anesthesia or nerve blockade which lasts for at least about one day after administration. Accordingly, the invention provides, in a first aspect, a drug delivery device for providing local analgesia, local anesthesia or nerve blockade at a site in a human or animal in need thereof, the device comprising a fibrillar collagen matrix; and at least one drug substance selected from the group consisting of amino amide anesthetics, amino ester anesthetics and mixtures thereof, the at least one drug substance being substantially homogeneously dispersed in the collagen matrix, and the at least one drug substance being present in an amount sufficient to provide a duration of local analgesia, local anesthesia or nerve blockade which lasts for at least about one day after administration.

It is hypothesized that such drug delivery devices as the bupivacaine-collagen sponge will afford post-operative pain management to patients without adverse effects associated with toxicity from the collagen sponge or elevated systemic anesthetic (such as bupivacaine) levels. It is hypothesized that such drug delivery devices as the bupivacaine-collagen sponge will provide local pain relief to patients for up to 48 or 72 hours at the surgical site and reduce the patient's demand for systemic analgesia and the associated adverse effects.

SUMMARY OF THE INVENTION

The present invention is directed to a drug delivery device for providing local analgesia, local anesthesia or nerve blockade at a site in a human or animal in need thereof, the device comprising a fibrillar collagen matrix; and at least one drug substance selected from the group consisting of amino amide anesthetics, amino ester anesthetics and mixtures thereof, the at least one drug substance being substantially homogeneously dispersed in the collagen matrix, and the at least one drug substance being present in an amount sufficient to provide a duration of local analgesia, local anesthesia or nerve blockade which lasts for at least about one day after administration. The present invention is directed, in an optional embodiment, to a biodegradable, leave-behind device.

BRIEF DESCRIPTION OF THE FIGURES

FIG. 1 shows, schematically, a flow diagram for the production of collagen.

FIG. 2 shows, schematically, a flow diagram for the production of a drug delivery device in the optional form of a bupivacaine-collagen sponge.

DETAILED DESCRIPTION OF THE INVENTION

This invention relates to a drug delivery device for providing local analgesia, local anesthesia or nerve blockade at a site in a human or animal in need thereof, the device comprising a fibrillar collagen matrix; and at least one drug substance selected from the group consisting of amino amide anesthetics, amino ester anesthetics and mixtures thereof the at least one drug substance being substantially homogeneously dispersed in the collagen matrix, and the at least one drug substance being present in an amount sufficient to provide a duration of local analgesia, local anesthesia or nerve blockade which lasts for at least about one day after administration.

In a second aspect, the invention relates to a method for providing local analgesia, local anesthesia or nerve blockade in a human or animal in need thereof, the method comprising administering at a site in a human or animal in need thereof a drug delivery device comprising a fibrillar collagen matrix; and at least one drug substance selected from the group consisting of amino amide anesthetics, amino ester anesthetics and mixtures thereof, the at least one drug substance being substantially homogeneously dispersed in the collagen matrix, and the at least one drug substance being present in an amount sufficient to provide a duration of local analgesia, local anesthesia or nerve blockade which lasts for at least about one day after administration.

Incorporation of the at least one drug substance selected from the group consisting of amino amide anesthetics, amino ester anesthetics and mixtures thereof in the fibrillar collagen matrix to provide the drug delivery device of the present invention delays the release of the at least one drug substance from the fibrillar collagen matrix and, thereby, prolongs the duration of local analgesia, local anesthesia or nerve blockade to at least about one day after administration of the drug delivery device.

By "site" or "surgical site" is meant the tissue(s) or organ(s) that is/are the intended aim of the surgical procedure, for example, around the now-removed uterus for hysterectomy as the surgical procedure.

Without being bound by theory, it is thought that the duration of local analgesia, local anesthesia or nerve blockade is prolonged by at least three times (optionally at least four times, further optionally at least five times) the duration of local analgesia, local anesthesia or nerve blockade that is achieved without being incorporated in the drug delivery device of the present invention.

Optionally, in the device or method of the invention, the at least one drug substance is present in an amount sufficient to provide a duration of local analgesia, local anesthesia or nerve blockade which lasts for at least about two days after administration.

Optionally, in the device or method of the invention, the at least one drug substance is present in an amount sufficient to provide a duration of local analgesia, local anesthesia or nerve blockade which lasts for at least about three days, further optionally at least four days, after administration.

The at least one drug substance is selected from the group consisting of amino amide anesthetics, amino ester anesthetics and mixtures thereof. Mixtures of amino amide anesthetics; mixtures of amino ester anesthetics; and mixtures of amino amide anesthetics and of amino ester anesthetics are specifically contemplated as forming part of the devices and methods of the present invention. In addition, optional devices and methods of the present invention may, in addition, contain one or more further drug substances, said one or more further drug substances not being amino amide anesthetics, amino ester anesthetics and mixtures thereof. Such further drug substances may comprise drugs efficacious in providing local analgesia, local anesthesia or nerve blockade.

Optionally, in the device or method of the invention, the at least one drug substance is an amino amide anesthetic selected from the group comprising Bupivacaine, Levobupivacaine, Lidocaine, Mepivacaine, Prilocalne, Ropivacaine, Articaine, Trimecaine and their salts and prodrugs. Further optionally, in the device or method of the invention, the at least one drug substance is an amino amide anesthetic selected from bupivacaine and salts and prodrugs thereof. Still further optionally, in the device or method of the invention, the at least one drug substance is an amino amide anesthetic selected from the group comprising Levobupivacaine, Lidocaine, Mepivacaine, Prilocalne, Ropivacaine, Articaine, Trimecaine and their salts and prodrugs.

Optionally, in the device or method of the invention, the fibrillar collagen matrix is a Type I collagen matrix.

Optionally, in the device or method of the invention, the fibrillar collagen matrix is a Type I collagen matrix and the at least one drug substance is an amino amide anesthetic selected from bupivacaine and salts and prodrugs thereof. Further optionally, the drug delivery device comprises a plurality of collagen sponges, each collagen sponge containing about 3.6 to about 8.0 mg/cm$^3$ type I collagen and about 2.0 to about 6.0 mg/cm$^3$ bupivacaine hydrochloride. Still further optionally, the drug delivery device comprises a plurality of collagen sponges, each collagen sponge containing about 5.6 mg/cm$^3$ type I collagen and about 4.0 mg/cm$^3$ bupivacaine hydrochloride.

Optionally, in the method of the invention, the method is for providing local analgesia, local anesthesia or nerve blockade in a human following laparotomy.

Optionally, in the method of the invention, the method is for providing local analgesia, local anesthesia or nerve blockade in a human following orthopedic, abdominal, gynecological or thoracic surgical procedures, such as benign abdominal or thoracic surgical procedures. Optionally, the benign abdominal or thoracic surgical procedures include benign gynecological procedures such as abdominal hysterectomies, myomectomy and adnexal surgery.

Optionally, in the method of the invention, the site in the human or animal in need thereof comprises a surgical site, such as a surgical site within a body cavity, for example, an abdominal or thoracic cavity. Further optionally, in the method of the present invention, a number of drug delivery devices of the present invention are placed at one or more sites of tissue disruption adjacent the surgical site, the number being such as to provide effective local analgesia, local anesthesia or nerve blockade in the human or animal in need thereof.

Optionally, in the method of the invention, the drug delivery device comprises a plurality of collagen sponges and wherein one sponge is divided between areas adjacent the surgical site, one sponge is divided and placed across the incision in the wall of the body cavity, for example the peritoneum, and one sponge is divided and placed between the sheath and skin around the incision.

Further optionally, in the method of the invention, the drug delivery device comprises a plurality of collagen sponges and wherein at least one sponge is placed adjacent the surgical site, optionally adjacent the site or sites of tissue disruption; at least one sponge is placed across the incision in the wall of the body cavity, for example the peritoneum (abdominal cavity wall); and at least one sponge is placed between the sheath and skin around the incision.

Still further optionally, in the method of the invention, the drug delivery device comprises a plurality of collagen sponges and wherein at least one sponge is placed adjacent the site or sites of tissue disruption such as one or more of the surgical site itself, skin, subcutaneous tissue, fascia, muscle and/or the parietal peritoneum.

Optionally, the total implanted dose is controlled according to the number and size of sponges administered and the location of the implanted sponges. Dosing is based on the principle that a surgeon implants one or more sponges on and around the various areas of tissue disruption. For example, in the case of abdominal or gastrointestinal (GI) surgery, sponges will be positioned below the skin incision and across the peritoneal incision. The number and size of sponges required (and hence the total dose of drug) will depend upon the type of surgical procedure and variables such as the size of the incision. For the overwhelming majority of routine surgical procedures, it is considered that sponges having a total surface area of up to 500 cm$^2$ (and a depth or thickness of 0.5 cm), for example sponges having a total surface area of up to 125 cm$^2$ (and a depth or thickness of 0.5 cm), will be sufficient to provide effective local analgesia, local anesthesia or nerve blockade to the areas of disrupted tissue.

Optionally, the dose employed in the method of the present invention can be tailored to a particular surgical procedure according to the extent of tissue disruption by varying the number and size of sponges implanted.

Optionally, the dose employed in the method of the present invention can be tailored to a particular surgical procedure according to the sites of tissue disruption by varying the location of the sponges to be implanted. Further optionally, the dose employed in the method of the present invention can be tailored to a particular surgical procedure according to the sites of tissue disruption, by placing the sponges to cover the tissue disruption, such as adjacent the sites of tissue disruption adjacent the surgical site, adjacent the incision in the wall of the body cavity, for example the peritoneum, and/or between the sheath and skin around the incision.

The suggested bupivacaine dosing regimens for the different abdominal surgeries are as follows:

Herniorrhaphy: sponges having a surface area of 50 cm$^2$ and a depth or thickness of 0.5 cm (100 mg bupivacaine hydrochloride)

Hysterectomy: sponges having a surface area of 75 cm$^2$ and a depth or thickness of 0.5 cm (150 mg bupivacaine hydrochloride)

GI surgery: sponges having a surface area of 75 or 100 cm$^2$ and a depth or thickness of 0.5 cm (150 or 200 mg bupivacaine hydrochloride)

The proposed maximum dose of 4 (each 5×5 cm with a thickness of 0.5 cm) sponges corresponds to a total bupivacaine hydrochloride dose of 200 mg. According to the package insert for USP Bupivacaine Injection, this marginally exceeds the standard bolus dose of 175 mg but is well within the recommended daily dose limit of 400 mg. It will, of course, be appreciated that the maximum number and size of implanted sponges (and, therefore, the drug dose) may vary according to the recommended daily dose limit for the drug or drugs in question.

Drug Substance

Suitable drug substances comprise amino amide anesthetics and amino ester anesthetics and their salts, hydrates and prodrugs. Such drug substances include, but are not limited to, amino amides such as Bupivacaine, Levobupivacaine, Lidocaine, Mepivacaine, Prilocalne, Ropivacaine, Articaine, Trimecaine and their salts and prodrugs; and amino esters such as Benzocaine, Chloroprocaine, Cocaine, Procaine, Tetracaine and their salts and prodrugs. Bupivacaine, and its salts and prodrugs is an optional drug substance. Mixtures of amino amides are contemplated, as are mixtures of amino esters. Mixtures of amino amides and amino esters are also contemplated.

Bupivacaine Hydrochloride (HCl) is a potent anesthetic and can produce moderate to prolonged anesthesia. When compared to other available amino amide anesthetics, the relatively longer duration of action coupled with its action on sensory block, rather than motor-block, permits prolonged anesthesia for post-operative pain. Bupivacaine HCl can provide effective sensory block and analgesia for several days. Bupivacaine HCl is indicated for moderate to prolonged local anesthesia and, therefore, treatment of moderate to acute pain.

Toxicity related to bupivacaine is caused by high systemic levels and is characterized by numbness of the tongue, light-headedness, dizziness and tremors, followed by convulsions and cardiovascular disorders.

The pharmacokinetics and pharmacodynamics of bupivacaine are well understood. Bupivacaine is about 95% bound to plasma proteins. Reported half-lives are from 1.5 to 5.5 hours in adults and about 8 hours in neonates. It is metabolized in the liver and is excreted in the urine, principally as metabolites with only 5 to 6% as unchanged drug. Bupivacaine is distributed into breast milk in small quantities. It crosses the placenta but the ratio of fetal to maternal concentrations is relatively low. Bupivacaine also diffuses into the cerebrospinal fluid (CSF).

The toxic threshold for bupivacaine plasma concentrations is considered to lie in the range of 2 to 4 micrograms/mL and, in the US, the maximum single recommended dose for anhydrous bupivacaine hydrochloride is 175 mg. Measurement of bupivacaine levels in the clinical setting needs to demonstrate dosing and systemic levels within these safety parameters. Thus, when it is suggested to administer bupivacaine, whether in one or several collagen sponges, it is suggested that the total dose should be no more than about 250 mg, optionally no more than about 200 mg, for anhydrous bupivacaine hydrochloride.

Collagen

Fibrillar collagen from different sources may be used including commercially available fibrillar collagen, for example, biomedical collagen from Devro Biomedical Collagen, Australia. Currently there are five known types of fibrillar collagen; Type I, II, III, V and XI. Alternatively, collagen can be extracted from tendons or hides of different animals, including horses, cattle, sheep and pigs. The attention of the skilled reader is drawn to Gelse et al (Advanced Drug Delivery Reviews 55 (2003), 1531-1546), the whole contents of which are incorporated herein by reference for further details on the various types of collagen. The present inventors have used a bovine-derived collagen Type I for the manufacture of bupivacaine-collagen sponges. Equine-derived collagen Type I is also suitable for use in the present invention, as are fibrillar collagen such as type I collagen from pigs and sheep. Type I collagen is a connective tissue extracted from animal tendons and other sources; in this case, the collagen is derived from bovine tendons. The Type I collagen consists of three approximately 1,050 amino-acid-long polypeptide chains, two alpha-I chains, and one alpha-2 chain. These are coiled to form a right-hand helix (known as a triple helix) around a common axis. The rod-shaped molecule has a length of 2900 Angstrom, a diameter of 14 Angstrom and a molecular weight of approx. 300,000 Daltons.

Method of Manufacture

The following general method of manufacture refers to type I collagen being produced from bovine tendons. However, alternative sources of fibrillar collagen such as alternative sources of type I or III collagen may be used in place of this methodology, without departing from the scope of the teaching of this invention.

The following general method of manufacture refers to bupivacaine as the drug substance. It will be appreciated that alternative drug substance(s), or additional drug substance(s) (i.e. additional to bupivacaine), may be used in place of bupivacaine alone, without departing from the scope of the teaching of this invention.

Collagen

Production of Type I Collagen from Bovine Tendons: The collagen is extracted from bovine Achilles tendon. During the manufacturing process, bovine tendons are first treated with 1N sodium hydroxide (NaOH) to clean and purify the material and to deplete the fat content followed by neutralization with 1N HCl. This step is followed by treatment with 0.9% sodium chloride (NaCl) solution to remove low molecular weight soluble components of the collagen. A treatment with hydrogen peroxide solution ensures bleaching of the tendons.

Reduction of the particle size of the collagen material is followed by fermentative breakdown using pepsin. Treatment with pepsin is used to degrade contaminating serum protein components, primarily bovine serum albumin and causes the detachment of non-helical portions of the collagen molecule (telopeptides). After filtration, precipitation of the collagen is accomplished by means of manipulation of the pH (from acidic pH to neutral pH). The fibrillar Type I collagen material is finally precipitated out of solution, washed again with distilled water to remove residual pepsin and then concentrated by means of centrifugation. The production process is outlined in FIG. 1.

Bupivacaine Collagen Sponge—Method of Manufacture

FIG. 2 is a flow diagram representing the production of the bupivacaine-collagen sponge. The skilled reader will appreciate that other drug substance(s) may be used in place of, or in addition to, the bupivacaine.

Compounding Process and Equipment

The fibrillar Type I collagen material prepared as in FIG. 1 is added to pre-heated water (below 42° C.) in a stainless steel (SS) vessel. Collagen swelling and subsequent dispersion formation is afforded by the use of a high-shear homogenizer. The homogenizer employed possesses a rotor-stator head that is designed to create high shear forces by pulling the collagen material through the rotating homogenizer head and forcing it against the proximal stationary stator head. It is this design that facilitates the high shear forces required to separate the fibrous collagen mass at the beginning of dispersion preparation.

Following completion of collagen dispersion formation, the dispersion is transferred to a closed heated jacketed vessel for final compounding. The jacket temperature is maintained at 36-38° C.

The or each drug substance (such as bupivacaine HCl) raw material is first dissolved in a portion of water at room temperature and is then introduced into the heat-jacketed SS vessel under low shear mixing to achieve homogeneity in the drug-loaded collagen dispersion. The collagen/bupivacaine dispersion is a free flowing opaque white to off-white liquid.

The dispersion is subsequently freeze-dried yielding a sponge containing, in one embodiment, 5.6 mg/cm$^3$ of collagen and 4.0 mg/cm$^3$ of bupivacaine HCl in a final lyophilized 5 cm×5 cm product. Other product sizes can also be manufactured including a 10 cm×10 cm sponge also containing, in an embodiment, 5.6 mg/cm$^3$ of collagen and 4.0 mg/cm$^3$ of bupivacaine HCl.

Filling/Lyophilization Process and Equipment

The collagen/drug dispersion is filled into appropriately sized lyophilization molds or blister trays for freeze-drying and the filling process is performed using a positive displacement pump. The pump is valve-less, has ceramic pistons and works on the principle of positive displacement.

Upon completion of tray filling, the filled moulds or blister trays are placed into the lyophilizer. Thermocouples are placed both in product and on shelves and a conductivity probe is also employed to provide in-process feedback on process temperatures and conductivity. The lyophilization process cycle used for the bupivacaine-collagen sponge involves freezing down to a temperature of −38° C. over 3.5 hours, followed by drying to a temperature of 30° C. over 14.5 hours.

Ethylene Oxide (EtO) Sterilization Process

The lyophilized sponge is packed into suitable packaging material, which may comprise of a sealed polyethylene blister or low density polyethylene (LDPE) sachet in an outer pouch consisting of polyethylene/LDPE laminate or aluminum foil. The product is then subjected to terminal sterilization, which can be gas-mediated ethylene oxide sterilization or radiation (gamma or electron beam). In the preferred embodiment, sterilization by ethylene oxide gas has been selected.

Ethylene oxide ($C_2H_4O$) is a gas at operating temperature and sterilizes via its action as a powerful alkylating agent. Under the correct conditions, cellular constituents of organisms such as nucleic acid complexes, functional proteins and enzymes will react with ethylene oxide, causing the addition of alkyl groups. As a result of the alkylation, cell reproduction is prevented and cell death ensues. Specific processing conditions and parameters must be met to achieve this effect within the target product; including but not limited to, acceptable concentration of ethylene oxide in the chamber and a minimum water activity level within the organism. The process is essentially a chemical reaction and is therefore temperature dependent; the rate of reaction increases with temperature. The optimum temperature is within the range of 30 and 40° C. These properties define the key characteristics of the ethylene oxide sterilization process.

The process is dependent on the water content existing in the sponges and a consistent range of moisture content is achieved by equilibration of the product with atmospheric humidity prior to sterilization. An optimum water content is not less than 9%. The product is loaded into stainless steel wire mesh baskets and placed into the stainless steel sterilizer chamber using a defined loading pattern. The sterilization chamber is then evacuated to remove air and ethylene oxide is introduced until the required concentration is achieved.

Product is held under these conditions for a defined period and, on completion of the pre-determined dwell period, ethylene oxide from the chamber is exhausted to the atmosphere via catalytic converters. These units ensure catalytic conversion of ethylene oxide to carbon dioxide and water with high efficiency. The sterilization chamber and its contents are then repeatedly flushed with air to remove the remaining ethylene oxide from the chamber. After completion of post sterilization flushing, the product is transferred to a holding area for longer term aeration. This phase of the process serves to further scavenge low level residual ethylene oxide from the product and packaging. The product is held at room temperature until the limits for ethylene oxide derivative residues have been reached.

Alternative Sterilization Process and Equipment

Radiation sterilization including gamma and electron beam may be used instead of the EtO sterilization process mentioned above.

The bupivacaine-collagen sponge manufactured under this general method of manufacture is a drug-delivery system composed of a Type I collagen matrix containing the amide local anesthetic bupivacaine HCl. The release of bupivacaine is primarily by dissolution and diffusion from the porous matrix with the collagen sponge acting as an inert delivery system.

Hysterectomies

Hysterectomy is the second most common surgery among women in the United States (US). According to the National Center For Health Statistics, there were 617,000 hysterectomies performed in the US in 2004. Indications for hysterectomy include benign tumors, such as fibroids, heavy periods, painful periods and chronic pelvic pain. The most common route for performing hysterectomy is through an incision in the abdominal wall; however, about 20% are performed vaginally. Laparoscopic-assisted vaginal hysterectomy is performed when warranted.

Pain Control after Surgery, Such as Hysterectomies

Effective postoperative pain management is important in ensuring that surgical subjects have a smooth and successful recovery after their operation. Pain after abdominal hysterectomy can be multifactoral. Incision pain, pain from deeper (visceral) structures, and particularly, dynamic pain, such as during straining, coughing, or mobilizing, can be quite severe. In one study, the authors found that visceral pain dominated during the first 48-hours after hysterectomy (Leung, 2000).

Morphine is often used via patient-controlled analgesic (PCA) pumps to control post-operative pain, but the large quantities required can lead to fatigue, nausea and vomiting, as well as the inability to mobilize because of drowsiness. Subjects usually require PCA for at least 24-hours, after which they receive oral analgesic drugs. The average postoperative narcotic consumption during the first 24-hours varies from 35 to 62 mg (Gupta, 2004) and the average postoperative morphine consumption using bupivacaine infiltration in both and superficial layers of the wound after abdominal hysterectomy was 54 mg (Klein et al, 2000) and 44 mg (Ng et al, 2002).

Collagen Products

The properties of insoluble and soluble collagen have led to its use in a variety of medical applications ranging from heart valves to dermal implants. Soluble collagen can be used to produce biodegradable or non-biodegradable materials that give useful mechanical properties and biocompatibility.

Soluble collagen can be cross-linked to produce semi-permanent, non-absorbable implants that can be delivered by intradermal injection such as those used in facial aesthetics. These were first approved by the US Food and Drug Administration (FDA) in the 1980s.

The present collagen matrix can be a localized drug delivery system based on a fibrillar (Type I or Type III) collagen matrix, optionally derived from bovine Achilles tendons. The products are manufactured as a lyophilized sponge.

Embodiments of the invention will now be demonstrated by reference to the above-mentioned General Method of Manufacture, which is then exemplified by reference to the Clinical Study described hereunder.

Specific embodiments of the invention will now be demonstrated by reference to the following general methods of manufacture and examples. It should be understood that these examples are disclosed solely by way of illustrating the invention and should not be taken in any way to limit the scope of the present invention.

EXAMPLES

Clinical Study

The effective relief of pain is of paramount importance to those treating patients undergoing surgery. This should be achieved for humanitarian reasons, but there is now evidence that pain relief has significant physiological benefit. Not only does effective pain relief mean a smoother postoperative course with earlier discharge from hospital, but it may also reduce the onset of chronic pain syndromes. Topical or local administration of anesthetics directly at the surgical site has the advantage of producing high local anesthetic concentrations, while minimizing potentially toxic systemic concentrations.

The bupivacaine-collagen sponge is highly malleable and can be applied directly, rolled or folded, giving the surgeon great flexibility in terms of application in wounds scheduled for closure.

Patients received three 5 cm×5 cm (×0.5 cm thick) sponges; one sponge divided between areas adjacent the surgical site (in this case, adjacent the location of the now-removed uterus), one sponge divided and placed across the incision in the wall of the body cavity (in this case, the peritoneum) and the final sponge divided and placed between the sheath and skin around the incision. Each sponge contained 50 mg of bupivacaine hydrochloride, giving a total dose of 150 mg per patient.

This was a single dose, open-label, prospective clinical study to investigate drug delivery devices in the form of a bupivacaine-collagen sponge in patients following hysterectomy, for pain control in hysterectomy. The patients were scheduled to receive a hysterectomy in the absence of uterine adenocarcinoma, cervical cancer, leiomyosarcoma or the suspicion of these cancers. Enrolled patients were to receive a total of three 5 cm×5 cm×0.5 cm bupivacaine-collagen sponges implanted at specified layers in the wound prior to wound closure. Each bupivacaine-collagen sponge was impregnated with 4 mg/cm$^3$ of bupivacaine.

Patient Selection Criteria
Inclusion
Aged between 18 to 60 years
60-95 Kg in weight
Able and willing to comply with pain relief regime outlined in the protocol
Exclusion
Known hypersensitivity to amide local anesthetics, NSAIDS, opioids and bovine collagen
Cardiac arrhythmias or AV conduction disorders
Concomitant use of other amide local anesthetics
Concomitant use of anti-arrhythmics e.g. Amiodarone
Concomitant use of propanolol
Spinal blockade
Concomitant use of strong/moderate CYP3A4 inhibitors or inducers e.g. macrolide antibiotics, grapefruit juice etc.
Previous major surgery in last 6 months
Hepatic impairment
Any clinically significant unstable cardiac, neurological, immunological, renal or haematological disease or any other condition that in the opinion of the Investigator would interfere with the course of the study
Participation in a clinical trial using an Investigational Product in the previous 6 months
Hemodynamically unstable at any point in the previous 4 weeks
Requirement for blood transfusion in the previous 3 months
Haemoglobin below 10 g/dL
Objectives
Objectives
   To investigate the potential analgesic effect of the bupivacaine-collagen sponge in the hysterectomy wound.
   To investigate the morphine sparing effect of using bupivacaine-collagen sponge as part of the post-operative analgesia regimen.
   To evaluate trends in numerical rating scales of pain intensity
The study outcomes comprise:
   Visual analogue pain rating scale (VAS)
   Morphine sparing effect
Study Duration
   Screening assessments (informed consent, medical history, vital signs, 12-lead electrocardiogram, clinical biochemistry and hematology, urinalysis and demographics) took place between 1 and 14 days prior to administration of the bupivacaine-collagen sponge. Baseline (0 hours) procedures included allocation of study number, baseline pain scoring and implantation of the sponge. Follow-up procedures took place over 96 hours post implantation. A follow-up call was performed 8 days after implantation.
Methodology
Safety Analysis
   Vital signs and clinical assessment for signs of systemic bupivacaine toxicity were repeated at 30 mins, 1, 1.5, 2, 3, 4, 5, 6, 9, 12 & 96 hours. A follow-up call was to be performed 8 days after surgery to check if the patient was suffering from any adverse event or is experiencing any problem with the wound. Concomitant medication (including doses of morphine and other pain medications) was collected from the screening until assessment 18.

TABLE 1

Safety Blood and Urinalysis Tests

| Haematology | Blood Chemistry | | Urinalysis |
| --- | --- | --- | --- |
| Haematocrit | Sodium | Total bilirubin | pH |
| Haemoglobin | Chloride | Direct bilirubin | Protein |
| RBC | Magnesium | ALT (SGPT) | Glucose |
| Platelet | Potassium | AST (SGOT) | Occult blood |
| WBC with differential | Calcium | Ferritin | |
| | Bicarbonate | Transferritin | |
| PT | Glucose | GGT | |
| PTT | Phosphorus | Iron | |
| | Uric Acid | C-reactive protein | |
| | Creatinine | Total Cholesterol | |
| | Blood Urea Nitrogen (BUN) | Triglycerides | |

Efficacy Evaluations
   Pain scoring using a visual analogue score (VAS) was used to assess the patient's experience of pain at 1, 1.5, 2, 3, 6, 9, 12, 18*, 24, 36, 48, 72 & 96 hour timepoints. Following surgery, patients were provided with PRN (per re nata, as needed) morphine via a PCA pump. Patient demand for morphine was recorded. *The pain assessment at 18 hours was optional so that sleep is not disturbed.

| LIST OF ABBREVIATIONS | |
|---|---|
| AE | Adverse Events |
| $AUC_{last}$ | Area under the plasma concentration-time curve from time zero to time t (time of last quantifiable plasma concentration) |
| $AUC_{inf}$ | Area under the plasma concentration-time curve from time zero to infinity |
| $C_{max}$ | Maximum plasma concentration |
| LOQ | Limit of quantification |
| PCA | Patient Controlled Analgesia |
| PRN | per re nata (as needed) |
| $t_{lag}$ | Lag-time |
| $t_{max}$ | Time of maximum plasma concentration |
| $t_{1/2}$ | Terminal half life |
| $\lambda_z$ | Terminal phase rate constant |
| VAS | Visual Analogue Scale |

Pain Control Medication (Supplemental to the Bupivacaine-Collagen Sponge)

At induction, patients received 50-75 µg fentanyl. Following catheterization and prior to the commencement of surgery, they also received 100 mg diclofenac rectally. Intra-operatively, morphine was administered intravenously as required to maintain adequate levels of analgesia. Post-operatively, patients received 1 g paracetamol six hourly, 50 mg diclofenac every 8 hours, with a maximum of 3 doses in any 24 hours, and morphine PRN (per re nata, as needed) using a patient controlled analgesia pump.

Concomitant Therapy
Permitted Concomitant Therapies

In order to ensure conformity in the amount of analgesia received post-operatively, all patients received 1000 mg paracetamol at 6 hourly intervals and 50 mg diclofenac at 8 hourly intervals and morphine PRN using a PCA pump.

Prohibited Concomitant Therapies

All analgesics were stopped for 24 hours prior to the study commencing. In addition, the following therapies (Table 2) were not administrated concomitantly with the implantation of the bupivacaine-collagen sponge.

TABLE 2

| Prohibited Concomitant Therapies | |
|---|---|
| Strong or Moderate Inhibitors of the CYP3A4 Pathway | Inducers of the CYP3A4 Pathway |
| Grapefruit juice | troglitazone |
| Methadone | phenytoin |
| Itraconazole | rifampicin |
| Ketoconazole | carbamazepine |
| Fluconazole | phenobarbal |
| Clarithromycin | St. John's Wort (hypericin) |
| Erythromycin | |
| Nefazodone | |
| Fluoxetine | |
| Ritonavir | |
| Indinavir | |
| Nelfinavir | |
| Amprenavir | |
| Saquinavir | |

Results
Safety Analysis
Current Safety Data from Clinical Study

| Pt No | AE Description | Causality | Severity | Treatment | Outcome |
|---|---|---|---|---|---|
| 001 | Urine infection | Unlikely | Moderate | No Antibiotics | Resolved by Day 8 |
| 001 | Nausea on 27 -01 | Unlikely | Moderate | Odensatron & ciclizine | resolved by Day 8 |
| 001 | Visual Disturbances | Possibly | Moderate | None | resolved by Day 8 |
| 001 | Raised white cell count | Unlikely | Mild | None | Resolved |
| 001 | Raised neutrophil count | Unlikely | Mild | None | Resolved |
| 002 | Nausea on 27 -01 | Unlikely | Mild | None | Resolved |
| 002 | 2 predose event: blood in urine, high ALT | — | — | — | — |
| 002 | Anemia | Unlikely | Mild | None | Resolved |
| 002 | High ALT | Possible | Mild | None | Resolved |
| 003 | Increased BP 1st few hours considered normal for patient & not significant | Unlikely | Moderate | None | Resolved by Day 2 |
| 003 | Raised C-reactive Protein | Unlikely | Moderate | None | Resolved |
| 004 | Anaemia HB 11 to 8 | Unlikely | Moderate | 2 Units blood transfusion | Hb 10 |
| 004 | Urine infection | Unlikely | Moderate | Augmentin 625 TDS 5 Days | Resolved |
| 004 | Blood in urine | Unlikely | Moderate | none | Unresolved |
| 004 | Raised C-reactive Protein | Unlikely | Moderate | None | Resolved |
| 005 | Bruising Around Abdomen | Possible | Moderate | None | Unresolved |
| 005 | Wheezing | Unlikely | Mild | None | resolved |
| 005 | Raised C-reactive Protein | Unlikely | Mild | None | Unresolved |

| Pt No | AE Description | Causality | Severity | Treatment | Outcome |
|---|---|---|---|---|---|
| 006 | Itchy chest and back with rash - urticaria | unknown | Moderate | Concomitant medication Required | Resolved |
| 006 | Anaemia | unknown | Mild | None | Resolved |
| 007 | Raised Phosphate | Possible | Mild | None | Resolved |
| 007 | Itchy skin on face, neck, right arm, feet - pruritus | Unlikely | Moderate | Concomitant medication Required | Resolved |
| 007 | wound infection | Unlikely | Moderate | Concomitant medication Required | Resolved |
| 007 | wound dehiscence | Unlikely | Mild | none | Resolved |
| 007 | Urine infection | Unlikely | Moderate | None | Resolved |
| 007 | Raised Phosphorus | Possible | Mild | None | Resolved |
| 007 | Diarrhoea | Unlikely | Moderate | None | Resolved |
| 007 | wound dehiscence | Unlikely | Moderate | Resuture under local anesthetic | Resolved |
| 008 | Lower back pain | Not related | Moderate | Concomitant medication Required | Resolved |
| 008 | Heat rash | Not related | Mild | None | Resolved |
| 008 | Rise of C-reactive protein | Unlikely | Mild | None | Resolving |
| 008 | Rise of White cell count | Unlikely | Mild | None | Resolved |
| 009 | Low platelet count | Unlikely | Moderate | None | Resolved |
| 009 | Raise of Phosphate | Unlikely | Mild | None | Resolved |
| 009 | Raise of ALT | Possible | Mild | None | Resolved |
| 009 | Raise of AST | Possible | Mild | None | Resolved |
| 010 | Low back pain | Unlikely | Mild | Concomitant medication Required | Resolved |
| 011 | Nausea, vomiting | Unlikely | +++ | Concomitant medication given: Cyclizine | Resolved |
| 011 | PT out of range | Unlikely | UN | None | Resolved |
| 012 | Nausea | Unlikely | Moderate | Concomitant medication given: Cyclizine | Resolved |
| 012 | Abdominal "wind" pain | Unlikely | Mild | None | Resolved |
| 012 | Low serum phosphate | Possible | Mild | None | Resolved |

Efficacy Analysis

Efficacy of the bupivacaine-collagen sponge was determined by use of visual analogue scales and by the morphine sparing effect.

Pain Scoring (Visual Analogue Pain Rating Scale)

Pain scoring using a visual analogue scale ranging from 0 (no pain) to 100 (worst imaginable pain). These were assessed from 1 hour onwards according to the assessment schedule. Individual pain scores were listed for each assessment time.

Morphine Sparing

Patients were given 6 hourly doses of 1000 mg paracetamol, 8 hourly doses of 50 mg diclofenac and morphine PRN via patient controlled analgesia (PCA) pump. The doses of morphine demanded by each patient over the first 24 hours of the treatment period were recorded and compared to historical data in the literature. Total doses of morphine required over the treatment period were listed for each patient.

12 subjects have, to date, been dosed and completed in this study. The total morphine usage and pain scores (Visual Analog Scale of 0 to 100 mm where 0 is no pain and 100 is the worst imaginable pain) that have been reported by these 12 subjects are presented in Tables 3 and 4.

Table 3 below shows that the average postoperative morphine consumption for the first 4 enrolled patients was 9 mg over the first 24 hours post-op. In contrast, the average postoperative morphine consumption using bupivacaine infiltration in both deep and superficial layers of the wound after abdominal hysterectomy was 54 mg (Klein et al, 2000) and 44 mg (Ng et al, 2002) and narcotic consumption during the first 24 hours varied from 35 to 62 mg (Gupta, 2004).

Morphine Sparing (PCA)

PCA morphine usage was collated over 24 hours and the average consumption was 16.8 mg (all 12 patients) (see Table 3 below). This mean value includes two outliers. One patient consumed 58 mg of morphine due to an underlying back condition and a second patient consumed 74 mg, who received non-standard anesthesia/analgesia during surgery. Without these two outliers, the mean morphine consumption was 7.1 mg. Literature data indicates morphine use ranging between 32 to 65 mg over the first 24 hours and the study data showing consumption of 31 to 99 mg morphine over 24 hours. Table 3 provides data on PCA morphine consumption for each patient.

Visual Analogue Scores (Pain)

The onset of pain relief occurred around 6 hours (mean VAS of 10.3 mm) and was maintained up to day of discharge (day 4-6) according to the VAS data. At 24 hours post-op, the mean score was 6.8 mm (25% of patients scored 0); at 48 hours it was 2.8 mm (7 of 12 patients scored 0) and at 72 hours the mean VAS was 2.7 mm and 50% of the patients scored 0 at this time-point. Several patients reported no pain even on application of pressure to the wound. Table 4 provides a summary of the VAS pain scores and Table 3 presents a table of individual pain scores and morphine consumption for all patients at key time-points.

TABLE 3

Summary of PCA Morphine Usage and Pain Scores of First 12 Subjects Enrolled in Ongoing Clinical Study

| | | Patient no | | | | | |
|---|---|---|---|---|---|---|---|
| | | 001 | 002 | 003 | 004 | 005 | 006 | 007 |
| Age | | 35 | 45 | 45 | 48 | 44 | 45 | 44 |
| Date of enrollment (date of surgery) | | 26 Jan. 2007 | 02 Feb. 2007 | 08 Feb. 2007 | 08 Feb. 2007 | 16 Feb. 2007 | 23 Mar. 2007 | 23 Mar. 2007 |
| Total Amount of Morphine consumed (mgs) | | 28 | 7 | 0 | 1 | 10 | 62 | 2 |
| VAS Pain scores (mm) | 1 h | 68 | 45 | 2 | 19 | 36 | 34 | 22 |
| | 1.5 h | 49 | 34 | 7 | 19 | 31 | 32 | 24 |
| | 2 h | 43 | 56 | 13 | 30 | 27 | 25 | 41 |
| | 3 h | 43 | 65 | 13 | 24 | 0 | 14 | 41 |
| | 6 h | 16 | 5 | 0 | 10 | 0 | 17 | 5 |
| | 9 h | 4 | 2 | 0 | 12 | 4 | 9 | 3 |
| | 12 h | 4 | 0 | 6 | 6 | 1 | 13 | 20 |
| | 18 h | ND | 0 | 4 | 6 | 8 | 65 | 24 |
| | 24 h | 14 | 3 | 2 | 4 | 0 | 25 | 1 |
| | 36 h | 24 | 2 | 3 | 0 | 21 | 11 | 0 |
| | 48 h | 2 | 0 | 0 | 0 | 7 | 3 | 0 |
| | 72 h | 1 | 9 | 0 | 0 | 2 | 11 | 6 |
| | 96 h | 0 | 6 | 0 | 0 | 1 | 7 | 11 |
| Day of discharge | | 5 | 4 | 5 | 5 | 6 | UNK | 4 |

| | | Patient no | | | | |
|---|---|---|---|---|---|---|
| | | 008 | 009 | 010 | 011 | 012 |
| Age | | 41 | 42.00 | 34 | 40 | 40 |
| Date of enrollment (date of surgery) | | 13 Apr. 2007 | 39206.00 | 11 May 2007 | 25 May 2007 | 13 Jul. 2007 |
| Total Amount of Morphine consumed (mgs) | | 57* | 15.00 | 2 | 74** | 0 |
| VAS Pain scores (mm) | 1 h | 48 | 5.32 | 0.00 | 100.00 | 17.02 |
| | 1.5 h | 55 | 0.00 | 47.87 | 72.34 | 18.09 |
| | 2 h | 34 | 29.79 | 28.72 | 80.85 | 17.02 |
| | 3 h | 21 | 50.00 | 29.79 | 84.04 | 9.57 |
| | 6 h | 12 | 14.89 | 10.64 | 34.04 | 2.13 |
| | 9 h | 2 | 10.64 | 12.77 | 34.04 | 1.06 |
| | 12 h | 2 | 3.19 | 13.83 | 23.40 | 5.32 |
| | 18 h | 8 | 1.06 | 7.45 | 21.28 | 14.89 |
| | 24 h | 0 | 0.00 | 3.19 | 26.60 | 3.19 |
| | 36 h | 0 | 0.00 | 3.19 | 4.26 | 2.13 |
| | 48 h | 0 | 0.00 | 0.00 | 22.34 | 1.06 |
| | 72 h | 0 | 0.00 | 0.00 | 2.13 | 0.00 |
| | 96 h | 0 | 0.00 | 0.00 | 0.00 | 0.00 |
| Day of discharge | | 6 | 6 | 5 | 5 | 4 |

*Patient suffered from an underlying lower back pain problem
**Patient received non-standard anesthesia/analgesia

TABLE 4

Summary of VAS Pain Scores: Efficacy Population

| Time Post Implantation (hours) | VAS Pain Score (mm) | | |
|---|---|---|---|
| | Mean | SD | Range |
| 1 | 33.5 | 29.3 | 0-100 |
| 1.5 | 31.6 | 20.1 | 0-72 |
| 2 | 34.7 | 17.5 | 13-81 |
| 3 | 32.0 | 23.7 | 0-84 |
| 6 | 10.3 | 9.3 | 0-34 |
| 9 | 7.9 | 9.2 | 0-34 |
| 12 | 7.9 | 7.4 | 0-23 |
| 18 | 14.4 | 18.4 | 0-65 |
| 24 | 6.8 | 9.5 | 0-27 |
| 36 | 5.8 | 8.4 | 0-25 |
| 48 | 2.8 | 6.1 | 0-22 |
| 72 | 2.7 | 3.9 | 0-11 |
| 96 | 2.2 | 3.7 | 0-11 |

Pharmacokinetics:

The mean $C_{max}$ was 0.22 µg/ml and the highest individual $C_{max}$ was 0.44 µg/ml, which is well below the known systemic toxicity level of 2-4 µg/ml for bupivacaine. The PK profile was similar for all patients and showed a decline in systemic levels after 24 hours. Table 5 provides a summary of the PK parameters.

TABLE 5

Summary of Bupivacaine Hydrochloride Pharmacokinetic Results: Efficacy Population

| Parameter | n | Mean | SD |
|---|---|---|---|
| $t_{lag}$ (h)* | 12 | 0.000 | 0.00-0.00 |
| $C_{max}$ (ng/mL) | 12 | 224.911 | 83.100 |
| $t_{max}$ (h)* | 12 | 12.000 | 0.53-24.00 |
| $\lambda_z$ (h$^{-1}$) | 11 | 0.07084 | 0.01307 |
| $t_{1/2z}$ (h) | 11 | 10.092 | 1.836 |
| $AUC_{last}$ (ng·h/mL) | 12 | 6531.2 | 2248.9 |
| $AUC_{inf}$ (ng·h/mL) | 11 | 6359.8 | 2230.1 |

Safety:

There were a total of 45 adverse events (AEs) reported by all patients, of which 44 were treatment-emergent. The majority of AEs reported in the study were not classified as being treatment-related, with only eight out of the 44 being deemed to be related. Of these, the majority were mild in severity and were all resolved. There was one serious adverse event reported during the study, which was moderate in severity and not related to the use of the Bupivacaine-containing drug delivery device of the present invention.

Conclusion:

The results of this trial are very encouraging and demonstrate pain relief coverage over the first 72 hours (and beyond) post-op according to VAS data. The low morphine use observed is a key feature for the drug delivery device of the present invention to facilitate recovery of the patient and to avoid debilitating narcotic side-effects.

EXAMPLE

Clinical Study-Dose Determination for Abdominal Hysterectomies and Other Non-Laparoscopic Benign Gynecological Procedures Such as Myomectomy and Adnexal Surgery The drug delivery device of the present invention is designed to provide prolonged, local analgesia by direct application of the drug delivery device to the site of tissue disruption. However, it should be emphasized that the drug delivery device of the present invention is not expected to provide complete relief from all postoperative pain or entirely eliminate the need for rescue analgesia medication but, instead, is intended as part of multimodal therapy for safe and effective pain management.

Each bupivacaine-containing drug delivery sponge has a surface area of 25 cm$^2$ (5×5 cm) and a thickness of approximately 0.5 cm. The active ingredient (bupivacaine hydrochloride) is homogenously dispersed throughout the collagen drug delivery matrix and, on a surface area basis, has a concentration of 2 mg/cm$^2$. This concentration targets the maximum achievable bupivacaine drug loading that still maintains the optimum physicochemical properties and performance attributes of the drug delivery device of the present invention; it corresponds to a weight ratio of 5 parts bupivacaine hydrochloride to 7 parts collagen.

Although the bupivacaine dose is fixed on a surface area basis, the total implanted dose is controlled according to the number of sponges administered and the location of administration of the sponges. Dosing is based on the principle that a surgeon implants the sponge on and around the areas of tissue disruption. For example, in the case of GI surgery, the sponge will be positioned below the skin incision and across the peritoneal incision. The number of sponges required (and hence the total dose of bupivacaine hydrochloride) will depend upon the type of surgical procedure and variables such as the size of the incision. For the overwhelming majority of routine surgical procedures, it is considered that sponges having a total surface area of up to 100 or 125 cm$^2$ and a thickness of 0.5 cm will be sufficient to adequately cover the areas of disrupted tissue.

The present inventors are studying efficacy in both moderate (herniorrhaphy) and major surgeries (total abdominal hysterectomy and open gastrointestinal surgery). The proposed dosing regimens for these different surgeries are as follows:

Herniorrhaphy: sponges having a total surface area of 50 cm$^2$ and a thickness of 0.5 cm (100 mg bupivacaine hydrochloride)

Hysterectomy: sponges having a total surface area of 75 cm$^2$ and a thickness of 0.5 cm (150 mg bupivacaine hydrochloride)

GI surgery: sponges having a total surface area of 75 or 100 cm$^2$ and a thickness of 0.5 cm (150 or 200 mg bupivacaine hydrochloride)

The proposed maximum dose of 4 (5×5 cm, with a thickness of 0.5 cm) sponges corresponds to a total bupivacaine hydrochloride dose of 200 mg. According to the package insert for USP Bupivacaine Injection, this marginally exceeds the standard bolus dose of 175 mg but is well within the recommended daily dose limit of 400 mg.

In summary, it is believed that the variable dosing regimens as provided by a fixed dose of 2 mg/cm$^2$ bupivacaine hydrochloride (50 mg/sponge; 5×5 cm, with a thickness of 0.5 cm) is justified for the following reasons when taking established safety, efficacy and product technology factors and principles into account:

i) The upper dose limit (on an mg/cm$^2$ basis) is primarily controlled by the drug delivery technology of the present invention. The potential for local analgesia at the site of tissue disruption using this technology is therefore maximized by having an optimally high drug loading in the drug delivery sponge of the present invention.

ii) The dose of the drug substance (such as bupivacaine) can be tailored to a particular surgical procedure according to the extent of tissue disruption by varying the number and size of sponges implanted.

iii) The dose of the drug substance (such as bupivacaine) can be tailored to a particular surgical procedure according to the sites of tissue disruption by varying the location of the sponges to be implanted.

iv) A maximum drug substance dose in sponges having a surface area of up to 500 cm$^2$ and a thickness of 0.5 cm provides sufficient coverage for the majority of moderate and major surgeries. A maximum bupivacaine dose in sponges having a surface area of up to 125 cm$^2$ and a thickness of 0.5 cm provides sufficient coverage for the overwhelming majority of moderate and major surgeries. The corresponding maximum dose of bupivacaine hydrochloride is 200 mg which, although it marginally exceeds the standard bolus dose, is well within the recommended daily dose (400 mg) for USP Bupivacaine Injection.

v) The bupivacaine-containing drug delivery sponge of the present invention is intended as part of multimodal therapy for the management of postoperative pain and is not expected to provide complete relief from postoperative pain or entirely eliminate the need for rescue medications. Clinical trials investigating lower drug loadings (i.e. less than 2 mg/cm$^2$) are therefore considered to be of limited value since the expected result is one of reduced patient benefit and a greater dependence on rescue medications.

The invention is not limited to the embodiments described and exemplified herein, which may be modified and amended without departing from the scope of the present invention. While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

REFERENCES

Gupta A, Perniola A, Axelsson K, Thorn S E, Crafoord K, and Rawal N (2004). Postoperative pain after abdominal hysterectomy: a double-blind comparison between placebo and local anesthetic infused intraperitoneally. Anesth Analg 99:1173-1179.

Leung C C, Chan Y M, Ngai S W, et al (2000). Effect of pre-incision skin infiltration on post-hysterectomy pain—a double-blind randomized controlled trial. Anaesth Intensive Care 2000; 28:510-516.

Ng A, Swami A, Smith G, et al (2002). The analgesic effects of intraperitoneal and incisional bupivacaine with epinephrine after total abdominal hysterectomy. Anesth Analg 2002; 95:158-162.

Sinclair et al, 1996 Postoperative pain relief by topical lidocaine in the surgical wound of hysterectomized patients; Acta Anaesthesiologica Scandinavica 40: 589-594

Hannibal et al, 1996 Preoperative wound infiltration with bupivacaine reduces early and late opioid requirements after hysterectomy. British Journal of Anaethesiology 83: 376-381

Cobby et al, 1997 Wound infiltration with local anaesthetic after abdominal hysterectomy British Journal of Anaethesiology: 78: 431-432

Victory et al, 1995 Effect of preincision versus postincision infiltration with bupivacaine on postoperative pain Journal of Clinical Anesthesia 7:192-196

Bartholdy et al, 1994 Preoperative infiltration of the surgical area enhances postoperative analgesia of a combined low-dose epidural bipivacaine and morphine regimen after upper abdominal surgery. Acta Anaesthesiologica Scandinavica 38: 262-265

Møiniche et al, 1998 A qualitative systemic review of incisional local anaesthesia for postoperative pain relief after abdominal operations; British Journal of Anaesthesia; 81: 377-383

Klein et al, 2000 Infiltration of the abdominal wall with local anaesthetic after total abdominal hysterectomy with no opioid-sparing effect; British Journal of Anaesthesia 84 (2): 248-9.

What is claimed is:

1. A drug delivery device for providing local analgesia, local anesthesia or nerve blockade at a site in a human or animal in need thereof, the device comprising a fibrillar collagen matrix; and at least one drug substance selected from the group consisting of amino amide anesthetics, amino ester anesthetics and mixtures thereof, the at least one drug substance being substantially homogeneously dispersed in the collagen matrix, and the at least one drug substance being present in an amount sufficient to provide a duration of local analgesia, local anesthesia or nerve blockade which lasts for at least about one day after administration.

2. The drug delivery device of claim 1, wherein the at least one drug substance is present in an amount sufficient to provide a duration of local analgesia, local anesthesia or nerve blockade which lasts for at least about two days after administration.

3. The drug delivery device of claim 1, wherein the at least one drug substance is present in an amount sufficient to provide a duration of local analgesia, local anesthesia or nerve blockade which lasts for at least about three days after administration.

4. The drug delivery device of claim 1, wherein the at least one drug substance is an amino amide anesthetic selected from the group comprising Bupivacaine, Levobupivacaine, Lidocaine, Mepivacaine, Prilocaine, Ropivacaine, Articaine, Trimecaine and their salts and prodrugs.

5. The drug delivery device of claim 1, wherein the at least one drug substance is an amino amide anesthetic selected from bupivacaine and salts and pro drugs thereof.

6. The drug delivery device of claim 1, wherein the fibrillar collagen matrix is a Type I collagen matrix.

7. The drug delivery device of claim 1, wherein the fibrillar collagen matrix is a Type I collagen matrix and the at least one drug substance is an amino amide anesthetic selected from bupivacaine and salts and prodrugs thereof.

8. The drug delivery device of claim 7, wherein the drug delivery device comprises a plurality of collagen sponges, each collagen sponge containing about 3.6 to about 8.0 mg/cm$^3$ type I collagen and about 2.0 to about 6.0 mg/cm$^3$ bupivacaine hydrochloride.

9. The drug delivery device of claim 7, wherein the drug delivery device comprises a plurality of collagen sponges, each collagen sponge containing about 5.6 mg/cm$^3$ type I collagen and about 4.0 mg/cm$^3$ bupivacaine hydrochloride.

10. A method for providing local analgesia, local anesthesia or nerve blockade in a human or animal in need thereof, the method comprising administering at a site in a human or animal in need thereof a drug delivery device comprising a fibrillar collagen matrix; and at least one drug substance selected from the group consisting of amino amide anesthetics, amino ester anesthetics and mixtures thereof, the at least one drug substance being substantially homogeneously dispersed in the collagen matrix, and the at least one drug substance being present in an amount sufficient to provide a duration of local analgesia, local anesthesia or nerve blockade which lasts for at least about one day after administration.

11. The method of claim 10, wherein the at least one drug substance is present in an amount sufficient to provide a duration of local analgesia, local anesthesia or nerve blockade which lasts for at least about two days after administration.

12. The method of claim 10, wherein the at least one drug substance is present in an amount sufficient to provide a duration of local analgesia, local anesthesia or nerve blockade which lasts for at least about three days after administration.

13. The method of claim 10, wherein the at least one drug substance is an amino amide anesthetic selected from the group comprising Bupivacaine, Levobupivacaine, Lidocaine, Mepivacaine, Prilocaine, Ropivacaine, Articaine, Trimecaine and their salts and prodrugs.

14. The method of claim 10, wherein the at least one drug substance is an amino amide anesthetic selected from bupivacaine and salts and prodrugs thereof.

15. The method of claim 10, wherein the fibrillar collagen matrix is a Type I collagen matrix.

16. The method of claim 10, wherein the fibrillar collagen matrix is a Type I collagen matrix and the at least one drug substance is an amino amide anesthetic selected from bupivacaine and salts and prodrugs thereof.

17. The method of claim 16, wherein the drug delivery device comprises a plurality of collagen sponges, each collagen sponge containing about 3.6 to about 8.0 mg/cm$^3$ type I collagen and about 2.0 to about 6.0 mg/cm$^3$ bupivacaine hydrochloride.

18. The method of claim 16, wherein the drug delivery device comprises a plurality of collagen sponges, each collagen sponge containing about 5.6 mg/cm$^3$ type I collagen and about 4.0 mg/cm$^3$ bupivacaine hydrochloride.

19. The method of claim 10, wherein the method is for providing local analgesia, local anesthesia or nerve blockade in a human following laparotomy.

20. The method of claim 10, wherein the method is for providing local analgesia, local anesthesia or nerve blockade in a human following orthopedic, abdominal, gynecological or thoracic surgical procedures.

21. The method of claim 17, wherein the method is for providing local analgesia, local anesthesia or nerve blockade in a human following orthopedic, abdominal, gynecological or thoracic surgical procedures.

22. The method of claim 18, wherein the method is for providing local analgesia, local anesthesia or nerve blockade in a human following orthopedic, abdominal, gynecological or thoracic surgical procedures.

23. The method of claim 10, wherein the drug delivery device comprises a plurality of collagen sponges and wherein at least one sponge is placed adjacent the surgical site, at least one sponge is placed across the incision in the wall of the body cavity and at least one sponge is placed between the sheath and skin around the incision.

* * * * *